US011191467B2

(12) United States Patent
Vollard-Derme et al.

(10) Patent No.: US 11,191,467 B2
(45) Date of Patent: Dec. 7, 2021

(54) METHOD AND A DEVICE FOR MONITORING THE CAPACITY OF A CREW MEMBER OF AN AIRCRAFT

(71) Applicant: Airbus Operations SAS, Toulouse (FR)

(72) Inventors: Cecile Vollard-Derme, Muret (FR); Laurent Barrou, Leguevin (FR); Jean Monfraix, Leguevin (FR); Benoît Papaïx, Toulouse (FR); Estelle Delpech, Plaisance-du-Touch (FR); Hafeda Remch, Toulouse (FR); Guillaume Chanel, St Julien en Genevois (FR); Daniel Lewkowicz, Toulouse (FR); Stanislas Boyer, Grenade (FR)

(73) Assignee: Airbus Operations SAS, Toulouse (FR)

( * ) Notice: Subject to any disclaimer, the term of this patent is extended or adjusted under 35 U.S.C. 154(b) by 154 days.

(21) Appl. No.: 16/456,542

(22) Filed: Jun. 28, 2019

(65) Prior Publication Data
US 2020/0000390 A1 Jan. 2, 2020

(30) Foreign Application Priority Data
Jul. 2, 2018 (FR) ...................................... 1856073

(51) Int. Cl.
*A61B 5/18* (2006.01)
*A61B 5/16* (2006.01)
(Continued)

(52) U.S. Cl.
CPC .............. *A61B 5/18* (2013.01); *A61B 5/0077* (2013.01); *A61B 5/01* (2013.01); *A61B 5/02055* (2013.01);
(Continued)

(58) Field of Classification Search
CPC ..... A61B 2503/22; A61B 5/0077; A61B 5/01; A61B 5/02055; A61B 5/02438;
(Continued)

(56) References Cited

U.S. PATENT DOCUMENTS 7,027,621 B1\* 4/2006 Prokoski ............ G06K 9/00248
180/272
7,801,591 B1\* 9/2010 Shusterman ........... A61B 5/352
600/509

(Continued)

FOREIGN PATENT DOCUMENTS

EP 3243430 A1 11/2017
WO 2017108548 A1 6/2017

*Primary Examiner* — Jonathan T Kuo
(74) *Attorney, Agent, or Firm* — Greer, Burns & Crain, Ltd.

(57) ABSTRACT

A monitoring device comprising at least one measurement module for measuring at least one physiological parameter of the crew member, at least one consolidation module for consolidating the measured physiological parameter or parameters, a fusion module for fusing the consolidated physiological parameter or parameters in order to detect at least one physiological status of the crew member, a filtering module for filtering the physiological status or statuses, a determination module for determining a level of incapacity of the crew member, a transmission module for transmitting a signal indicative of the level of incapacity of the crew member to a user device.

13 Claims, 2 Drawing Sheets

(51) Int. Cl.
  *A61B 5/00* (2006.01)
  *A61B 5/01* (2006.01)
  *A61B 5/0205* (2006.01)
  *A61B 5/11* (2006.01)
  *G16H 50/30* (2018.01)
  *G16H 50/70* (2018.01)
  *G16H 50/20* (2018.01)
  *G06N 7/00* (2006.01)
  *A61B 5/024* (2006.01)

(52) U.S. Cl.
  CPC ........... *A61B 5/1103* (2013.01); *A61B 5/1114* (2013.01); *A61B 5/1128* (2013.01); *A61B 5/163* (2017.08); *A61B 5/6803* (2013.01); *A61B 5/7275* (2013.01); *A61B 5/7278* (2013.01); *G06N 7/005* (2013.01); *G16H 50/20* (2018.01); *G16H 50/30* (2018.01); *G16H 50/70* (2018.01); *A61B 5/02438* (2013.01)

(58) Field of Classification Search
  CPC ....... A61B 5/0402; A61B 5/0476; A61B 5/08; A61B 5/1102; A61B 5/1103; A61B 5/1114; A61B 5/1116; A61B 5/1128; A61B 5/163; A61B 5/18; A61B 5/6803; A61B 5/6816; A61B 5/6888; A61B 5/7275; A61B 5/7278; G06N 7/005; G16H 40/63; G16H 50/00–50/80; G08B 21/00–21/0211
  See application file for complete search history.

(56) References Cited

U.S. PATENT DOCUMENTS

| | | | |
|---|---|---|---|
| 10,172,566 B2* | 1/2019 | Papaix | A61B 5/18 |
| 10,786,693 B1* | 9/2020 | Opperman | A61B 5/7275 |
| 2007/0100666 A1* | 5/2007 | Stivoric | A61B 5/6833 |
| | | | 705/3 |
| 2008/0122636 A1 | 5/2008 | Matos | |
| 2014/0240132 A1* | 8/2014 | Bychkov | A61B 5/18 |
| | | | 340/576 |
| 2015/0257681 A1 | 9/2015 | Shuster et al. | |
| 2017/0325701 A1 | 11/2017 | Castro Miller et al. | |
| 2017/0332975 A1* | 11/2017 | Papaix | G06N 7/005 |
| 2018/0360387 A1 | 12/2018 | Bulut et al. | |

* cited by examiner

METHOD AND A DEVICE FOR MONITORING THE CAPACITY OF A CREW MEMBER OF AN AIRCRAFT

CROSS-REFERENCES TO RELATED APPLICATIONS

This application claims the benefit of the French patent application No. 1856073 filed on Jul. 2, 2018, the entire disclosures of which are incorporated herein by way of reference.

FIELD OF THE INVENTION

The present invention relates to a method and a device for monitoring the capacity of a crew member in an aircraft.

BACKGROUND OF THE INVENTION

The capacity of a crew member may be one of the criteria that allow a flight to be made under favorable conditions.

Monitoring the capacity of a crew member makes it possible to detect incapacity of the crew member. Incapacity is defined as corresponding to a degradation in the psychophysiological state of the pilot. This psychophysiological state is generally caused by psychological or physiological medical events that the crew member has experienced. Incapacity may manifest itself in various forms. For example, it may come on suddenly and completely in the form of an infarction or more subtly and partially in the form of a state of fatigue. Incapacity of a crew member can be detected only by the crew member himself or by another crew member. This means that it is sometimes difficult to detect certain types of incapacity of a crew member.

At the present time, there is no technical means for precisely detecting the incapacity of a crew member during the flight of an aircraft.

SUMMARY OF THE INVENTION

It is an object of the present invention to alleviate these disadvantages by proposing a method and a device that make it possible to detect incapacity of a crew member by monitoring the capacity of the crew member.

To this end, the invention relates to a method for monitoring the capacity of a crew member of an aircraft.

According to the invention, the method comprises the following steps:

a measurement step, which is implemented by at least one measurement module, comprising measuring at least one physiological parameter regarding the crew member and in supplying at least one associated confidence score to the measurement module or modules respectively;

a consolidation step, which is implemented by at least one consolidation module, comprising consolidating the measured physiological parameter or parameters and in determining one or more consolidated confidence scores regarding the consolidated physiological parameter or parameters;

a fusion step, which is implemented by a fusion module, comprising fusing the consolidated physiological parameter or parameters so as to detect at least one physiological status of the crew member from at least one physiological status detection function;

a filtering step, which is implemented by a filtering module, comprising filtering the physiological status or statuses detected in the fusion step so as to retain the most probable physiological status or statuses;

a determination step, which is implemented by a determination module, comprising determining a level of incapacity of the crew member from the most probable physiological status or statuses determined in the filtering step;

a transmission step, which is implemented by a transmission module, comprising transmitting to a user module a signal indicative of the level of incapacity of the crew member.

Thus, by virtue of the invention, it is possible to detect incapacity of the crew member by measuring physiological parameters so that an action plan can be implemented, if necessary.

According to a first particular feature, the fusion step comprises substeps of a first detection function, including:

a first comparison substep, which is implemented by a first comparison submodule, comprising comparing at least one consolidated physiological parameter against at least one predetermined incapacity threshold;

a first determination substep, which is implemented by a first determination submodule, comprising determining at least a first physiological status on the basis of the result of the comparison of the first comparison substep.

According to a second particular feature, the fusion step comprises substeps of a second detection function, including:

a second determination substep, which is implemented by a second determination submodule, comprising determining at least a second physiological status from at least one consolidated physiological parameter and from an inference system comprising conditional rules and probability densities, the conditional rules and the probability densities being based on medical experiments and analysis of medical data.

According to a third particular feature, the fusion step comprises substeps of a third detection function, including:

a first computation substep, which is implemented by a first computation submodule, comprising computing a probability of good health, the probability of good health corresponding to a probability of a crew member in good health encountering the consolidated physiological parameter or parameters;

a second comparison substep, which is implemented by a second comparison submodule, comprising comparing the probability of good health against at least one predetermined good health threshold;

a third determination substep, which is implemented by a third determination submodule, comprising determining at least one third physiological status on the basis of the result of the comparison of the second comparison substep.

In addition, the filtering step comprises the following substeps:

a second computation substep, which is implemented by a second computation submodule, comprising computing a mean of the confidence score or scores for each of the physiological status detection functions, the confidence score or scores being associated with the measurement module or modules configured to measure the physiological parameter or parameters used by the physiological status detection function;

a third comparison substep, which is implemented by a third comparison submodule, comprising comparing the mean calculated in the second computation substep against a predetermined confidence score threshold;

a fourth determination substep, which is implemented by a fourth determination submodule, comprising determining the most probable physiological status or statuses on the basis of the result of the comparison of the third comparison substep.

According to one embodiment, the measurement step comprises the following substeps:

a substep of measuring fatigue, which is implemented by a first fatigue measurement module located in a headset configured to be donned by the crew member and by a second fatigue measurement module located in a first video equipment configured to capture images of the crew member, comprising capturing measurements of the fatigue of the crew member;

a substep of measuring cardiac rhythm, which is implemented by a first cardiac rhythm measurement module located in the headset, a second cardiac rhythm measurement module located in the first video equipment and a third cardiac rhythm measurement module located in a seat configured to accept the crew member, comprising capturing measurements of the cardiac rhythm of the crew member;

a substep of measuring body temperature, which is implemented by a first body temperature measurement module located in the headset, a second body temperature measurement module located in the first video equipment and a third body temperature measurement module located in the seat, comprising capturing measurements of the body temperature of the crew member;

a substep of measuring head orientation, which is implemented by a first head orientation measurement module located in the headset and a second head orientation measurement module located in the first video equipment, comprising capturing measurements of the orientation of the head of the crew member;

a substep of measuring head movement, which is implemented by a first head movement measurement module located in the headset and a second head movement measurement module located in the first video equipment, comprising capturing measurement of the movements of the head of the crew member;

a substep of measuring blink rate, which is implemented by an ocular measurement module located in the first video equipment, comprising capturing measurements of the frequency at which the crew member blinks;

a substep of measuring presence, which is implemented by a presence measurement module located in the first video equipment, comprising capturing measurements of the presence of the crew member;

a substep of measuring movement, which is implemented by a movement measurement module located in the seat, comprising capturing measurements of the movement of the crew member.

Advantageously, the fatigue measurement substep is also implemented by a third fatigue measurement module located in a seat configured to accept the crew member.

In addition, the consolidation step comprises the following substeps:

a substep of consolidating the measured fatigue, which is implemented by a first consolidation submodule, comprising determining a consolidated fatigue measurement from the fatigue measurements captured in the fatigue measurement substep;

a substep of consolidating the measured cardiac rhythm, which is implemented by a second consolidation submodule, comprising determining a consolidated measurement for cardiac rhythm from the cardiac rhythm measurements captured in the cardiac rhythm measurement substep;

a substep of consolidating the measured body temperature, which is implemented by a third consolidation submodule, comprising determining a consolidated body temperature measurement from the body temperature measurements captured in the body temperature measurement substep;

a substep of consolidating the measured head orientation, which is implemented by a fourth consolidation submodule, comprising determining a consolidated head orientation measurement from the head orientation measurements captured in the head orientation measurement substep;

a substep of consolidating measured head movement, which is implemented by a fifth consolidation submodule, comprising determining a consolidated head movement measurement from the head movement measurements captured in the head movement measurement substep.

Furthermore, the substeps of the first detection function are implemented in respect of the consolidated physiological parameter corresponding to the consolidated fatigue measurement, the first physiological status corresponding to a fatigue status, the consolidated fatigue measurement being compared against a first predetermined incapacity threshold in the first comparison substep.

Moreover, the substeps of the first detection function are implemented in respect of the consolidated physiological parameters corresponding to the consolidated body temperature measurement and to the consolidated cardiac rhythm measurement, the first physiological statuses corresponding to a febrile status and to a cardiac status, the consolidated body temperature measurement being compared against a second predetermined incapacity threshold in the first comparison substep, the consolidated cardiac rhythm measurement being compared against a third predetermined incapacity threshold in the first comparison substep.

In addition, the substeps of the third detection function are implemented in respect of the consolidated physiological parameters corresponding to the consolidated body temperature measurement and to the consolidated cardiac rhythm measurement, the third physiological statuses corresponding to a febrile status and to a cardiac status, the probability of good health for the consolidated body temperature measurement being compared against a first predetermined good health threshold in the second comparison substep, the probability of good health for the consolidated cardiac rhythm measurement being compared against a second predetermined good health threshold in the second comparison substep.

In addition, the substeps of the second detection function are implemented in respect of the consolidated physiological parameters corresponding to the consolidated head orientation measurement, to the consolidated head movement measurement, to the consolidated presence measurement and to the consolidated blink rate measurement, the second physiological status corresponding to a first consciousness level status.

In addition, the substeps of the third detection function are implemented in respect of the consolidated physiological parameters corresponding to the consolidated head orientation measurement, to the consolidated head movement measurement, to the consolidated presence measurement and to the consolidated blink rate measurement, the third physiological status corresponding to a second consciousness level status, a first probability of good overall health being determined in the first computation substep from a probability of good health for the consolidated head orientation measurement, a probability of good health for the consolidated head movement measurement, a probability of good health for the consolidated presence measurement and a probability of good health for the consolidated blink rate measurement, the first probability of overall good health being compared in the second comparison substep against a first predetermined overall good health threshold.

In addition, the substeps of the third detection function are implemented in respect of the consolidated physiological parameters corresponding to the fatigue measurement, to the body temperature measurement, to the cardiac rhythm measurement, to the consolidated head orientation measurement, to the consolidated head movement measurement, to the consolidated presence measurement, to the consolidated blink rate measurement and to the measurement of the movement of the crew member, the third physiological status corresponding to a crew member incapacity status, a second probability of overall good health is determined in the first computation substep from a probability of good health for the consolidated body temperature measurement, a probability of good health for the consolidated cardiac rhythm measurement, a probability of good health for the consolidated head orientation measurement, a probability of good health for the consolidated head movement measurement, a probability of good health for the consolidated presence measurement, a probability of good health for the consolidated blink rate measurement and a probability of good health for the consolidated measurement of the movement of the crew member, the second probability of overall good health being compared in the second comparison step against a second predetermined overall good health threshold.

The invention also relates to a device for monitoring the capacity of a crew member of an aircraft.

According to the invention, the device comprises:

at least one measurement module, configured to measure at least one physiological parameter regarding the crew member and to supply at least one associated confidence score to the measurement module or modules respectively;

at least one consolidation module, configured to consolidate the measured physiological parameter or parameters and to determine the consolidated confidence score or scores regarding the consolidated physiological parameter or parameters;

a fusion module, configured to fuse the consolidated physiological parameter or parameters in order to detect at least one physiological status of the crew member from at least one physiological status detection function;

a filtering module, configured to filter the physiological status or statuses detected by the fusion module in order to retain the most probable physiological status or statuses;

a determination module, configured to determine a level of incapacity of the crew member from the most probable physiological status or statuses determined by the filtering module;

a transmission module, configured to transmit to a user module a signal indicative of the level of incapacity of the crew member.

The invention also relates to an aircraft, particularly a transport airplane, which comprises a device for monitoring the capacity of a crew member, as specified hereinabove.

BRIEF DESCRIPTION OF THE DRAWINGS

The invention, together with its features and advantages, will become more clearly apparent from reading the description given with reference to the attached drawings in which:

FIG. 3 depicts an aircraft carrying the monitoring device.

DETAILED DESCRIPTION OF THE PREFERRED EMBODIMENTS

Figure 1:
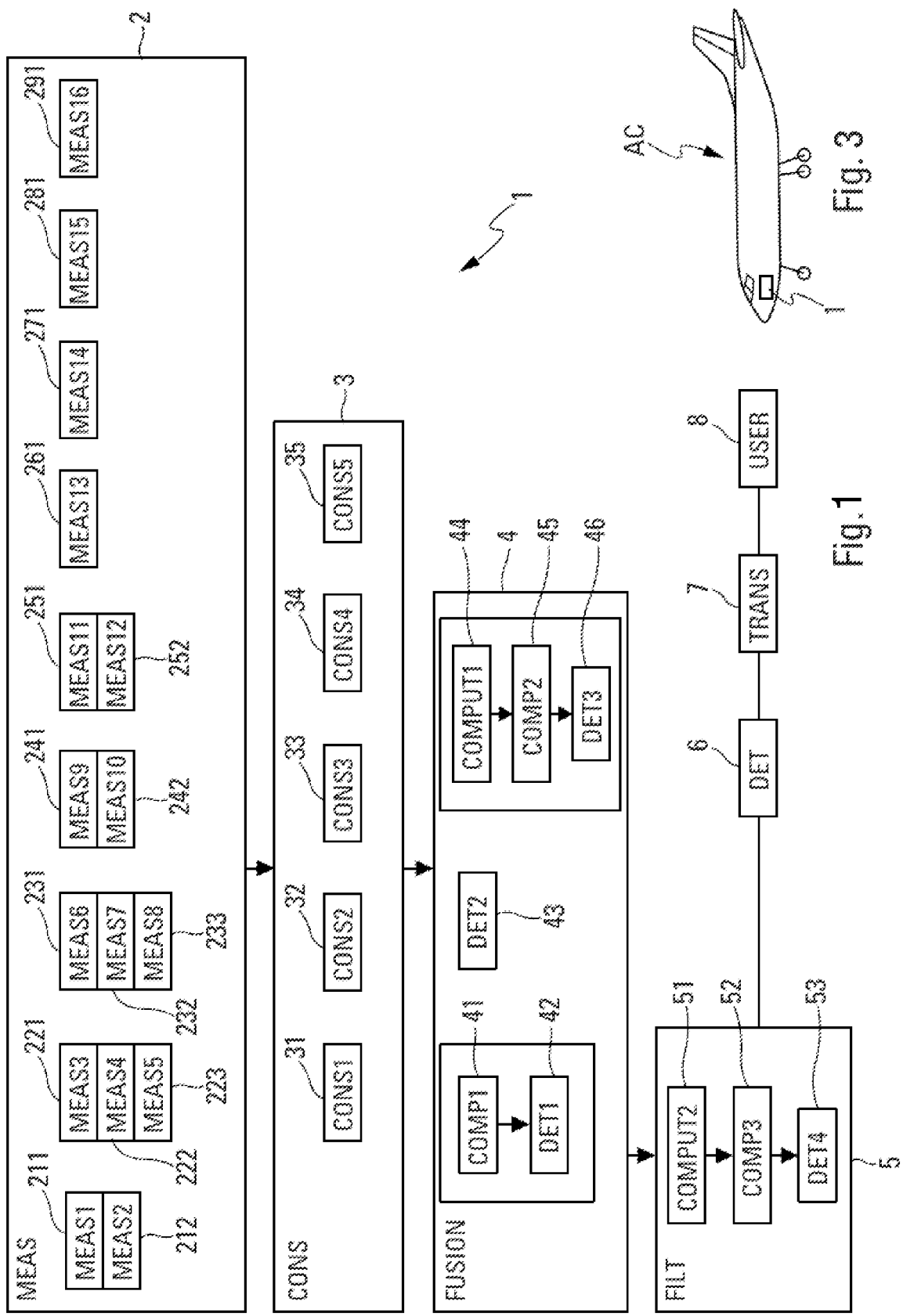
FIG. 1 depicts one embodiment of the monitoring device.

The device 1 for monitoring the capacity of a crew member of an aircraft AC is depicted in FIG. 1. In the remainder of the description, the device 1 for monitoring the capacity of a crew member of an aircraft AC will be referred to as a "monitoring device." The crew member may correspond to the pilot of the aircraft AC.

The monitoring device 1 carried on the aircraft AC (FIG. 3) comprises at least one measurement module MEAS 2. The measurement module or modules are configured to measure at least one physiological parameter regarding the crew member and to supply at least one associated confidence score to the measurement module or modules respectively.

According to one preferred embodiment, the measurement module comprises a set of measurement modules 2 contained in a headset (boomset) configured to be donned by the crew member, in a seat configured to accept the crew member and in a video equipment configured to capture images of the crew member.

In this preferred embodiment, the headset comprises a module 211 for measuring fatigue MEAS1, a module 221 for measuring cardiac rhythm MEAS3, a module 231 for measuring body temperature MEAS6, a module 241 for measuring head orientation MEAS9, a module 251 for measuring head movement MEAS11 and, possibly, a module for measuring respiratory rhythm.

The cardiac rhythm measurement module 221 is mounted on the headset so that it is situated in a region of the forehead or of the temples of the crew member wearing the headset. Advantageously, the cardiac rhythm measurement module 221 uses the principle of photoplethysmography.

The fatigue measurement module 211 comprises electroencephalogram probes and a fatigue level computation unit. The probes are configured to measure electrical activity in the brain of the crew member, particularly beta, alpha, theta and delta waves. For example, two probes are mounted in the headset in such a way that the first probe, referred to as the Cz probe, is situated on the vertex of the skull of the crew member wearing the headset and the second probe, referred to as the Pz probe, is situated on the skull approximately 10 cm behind the vertex. Other regions may be covered according to the desired measurements. Advantageously, the probes are dry probes in order to make the headset easier to use and in order to avoid the use of consumable products such as mousses or gels. The computation unit makes it possible, using an algorithm, to determine the level of fatigue of the crew member wearing the headset from the data supplied by the probes.

The body temperature measurement module 231 comprises a first sensor mounted on the headset in such a way that it is positioned in the region situated behind the ear lobe of the crew member wearing the headset. Specifically this is because this region provides a very stable measurement of body temperature because this region is not very susceptible to variations in temperature. The body temperature measurement module 231 may equally be mounted on the headset in such a way that it is situated in the region of the temples of the crew member wearing the headset. Advantageously, the body temperature measurement module 231 employs the principle of infrared reflectometry. Given that the measurements taken using this principle are dependent on the distance between the sensor and the skin of the crew member, a mechanical adapter may be employed in order to provide a constant setting for that distance when the headset is donned. The body temperature measurement module 231 may also comprise a second sensor for ambient temperature. The ambient temperature measurement allows the temperature measurements of the first sensor to be adjusted in order to obtain a more precise body temperature measurement.

The head orientation measurement module 241 and the head movement measurement module 251 form an inertial measurement unit. The inertial measurement unit has six degrees of freedom through the combination of a gyrometer, of an accelerometer and of a magnetometer, providing the attitude of the head about the axes of pitch, roll and yaw, the linear acceleration of the head along the three axes and the linear speed of the head along the three axes. The head orientation and the head movements can then be deduced from these.

In the preferred embodiment, the video equipment comprises a module 261 for taking ocular measurements MEAS13, a module 212 for measuring fatigue MEAS2, a module 222 for measuring cardiac rhythm MEAS4, a module 242 for measuring head orientation MEAS10, a module 232 for measuring body temperature MEAS7, a module 252 for measuring head movement MEAS12, a module 271 for measuring presence MEAS14 and, possibly, a module 291 for measuring normality MEAS16. The video equipment may also comprise a module for measuring respiratory rhythms.

A normality measurement may correspond to a measurement indicative of the normality of a scene captured by a video sensor.

The video equipment may comprise at least one camera and infrared lighting so as to improve detection capabilities. Advantageously, the camera or cameras are positioned in such a way that the camera or cameras can record at least the eyes of the crew member under different crew configurations. The modules of the video equipment are configured to measure various parameters relating to the crew member.

For example, the ocular measurement module 261 is able to measure at least one of the following parameters:
the gaze,
measurements associated with the eye and parts of the eye (iris, pupil, etc.) such as closings of the eye, blinking, diameter, etc.,
the facial expression (joy, anxiety, sadness, etc.).

The head orientation measurement module 242 is able to measure the position of the head (Euler angles)

The head movement measurement module 252 can measure the movements of the head and yawning.

The cardiac rhythm measurement module 222 can measure the cardiac rhythm of the crew member.

The body temperature measurement module 232 can measure the body temperature of the crew member.

The presence measurement module 271 can measure the presence or non-presence of the crew member on his seat or else in the flight deck (cockpit) but not in his seat, or else outside the cockpit.

The fatigue measurement module 212 may comprise a video data analysis unit. This video data analysis unit makes it possible, for example, to determine a level of fatigue of the crew member using an algorithm configured to compute parameters such as a PERcentage of eyelid CLOSure over the pupil over time (PERCLOS).

The respiratory rhythm module may comprise another video data analysis unit to determine the respiratory rhythm measurement. The video data may be supplied by an infrared camera. The seat may also comprise at least one respiratory rhythm measurement module.

The modules of the video equipment are able to operate under various cockpit lighting conditions (day, night, dusk, etc.) and under various crew member face lighting conditions (half lit, lit horizontally or vertically). The ocular measurement module 261 may also operate normally for crew members wearing any type of sunglasses.

In the preferred embodiment, the seat comprises a module 223 for measuring cardiac rhythm MEAS5, a module 233 for measuring body temperature MEAS8, a module 281 for measuring movement MEAS15 (body movement). The seat may also comprise at least one fatigue measurement module (not depicted).

The modules contained in the seat may comprise sensors located at suitable points for measuring cardiac rhythm, respiratory rhythm, body temperature, posture of the crew member, the body movements of the crew member and his or her presence.

For example, the cardiac rhythm measurement module 223 comprises sensors of the electrocardiogram type employing electrodes for cardiac rhythm, cardiac cycle, respiratory rhythm and actimetry. As far as the respiratory (respiration) rhythm measurement is concerned, a sensor may be incorporated into the seat by using, for example, a ballistocardiography (BCG) or capacitive electrocardiography (c-ECG) technique.

The body temperature measurement module 233 may comprise temperature sensors such as thermocouples, electrical-resistance detection sensors or silicon bandgap temperature sensors.

The sensors may be located at various points such as:
at the top of the seat cushions,
built into a seat cover,
under the seat cover,
built into the foam of the cushions,
under the cushions.

A first fatigue measurement module contained in the seat may use pressure sensors to determine a postural attitude of the crew member. A second fatigue measurement module may be built into a headrest of the seat. This second fatigue measurement module may use an electroencephalogram (EEG) sensor.

The monitoring device 1 further comprises at least one consolidation CONS module 3. The consolidation module 3 is configured to consolidate the measured physiological parameter or parameters and to determine the consolidated confidence score or scores regarding the consolidated physiological parameter or parameters.

The consolidation module 3 makes it possible to ensure the robustness and reliability of the information obtained from the measurements, in order to mitigate the effect of failure of a sensor or inaccuracy of a sensor.

A consolidation function takes the following form:

$$C(\langle s_1, cs_1 \rangle, \ldots, \langle s_n, cs_n \rangle) = \langle S, CS \rangle,$$

in which:
$s_i$ corresponds to the measurement supplied by a sensor i,
$cs_i$ corresponds to the confidence score for the measurement supplied by the sensor i,
S corresponds to the consolidated measurement, CS corresponds to the confidence score for the consolidated measurement.

Each consolidation function can be obtained automatically using machine learning techniques, such as neural networks or decision trees. It may take the form of a linear (or some other) combination, of conditional rules, of a neural graph containing activation functions, etc.

According to the preferred embodiment, the consolidation module 3 comprises the following submodules:

a consolidation CONS1 submodule 31 configured to determine a consolidated fatigue measurement from the fatigue measurements captured by the fatigue measurement modules 211, 212, a consolidation CONS2 submodule 32 configured to determine a consolidated cardiac rhythm measurement from the cardiac rhythm measurements captured by the cardiac rhythm measurement modules 221, 222, 223, a consolidation CONS3 submodule 33 configured to determine a consolidated body temperature measurement from the body temperature measurements captured by the body temperature measurement modules 231, 232, 233, a consolidation CONS4 submodule 34 configured to determine a consolidated head orientation measurement from the head orientation measurements captured by the head orientation measurement modules 241, 242, a consolidation CONS5 submodule 35 configured to determine a consolidated head movement measurement from the head movement measurements captured by the head movement measurement modules 251, 252.

The monitoring device 1 also comprises a fusion FUSION module 4 configured to fuse the consolidated physiological parameter or parameters in order to detect at least one physiological status of the crew member from at least one physiological status detection function.

The physiological status or statuses may correspond to one or more physiological states or to one or more psychological and physiological states of the crew member. For example, the physiological statuses may correspond to a state of fatigue, a feverous state, a cardiac state or a consciousness level state.

The physiological status or statuses may adopt binary values indicating the physiological state of the crew member. For example, a physiological status corresponding to a state of fatigue adopting a binary value equal to 1 indicates that the crew member is considered to be suffering from fatigue. If this physiological status adopts a value equal to 0, that indicates that the crew member is not considered to be suffering from fatigue.

The fusion module 4 may comprise submodules implementing a first detection function including:

a comparison COMP1 submodule 41 configured to compare at least one consolidated physiological parameter against at least one predetermined incapacity threshold;

a determination DET1 submodule 42 configured to determine at least a first physiological status on the basis of the result of the comparison obtained by the comparison submodule 41.

The predetermined incapacity threshold or thresholds correspond to expert thresholds based on medical experiments and medical data analysis. The purpose of these is to determine when a consolidated physiological parameter adopts a value indicating a symptom of a given incapacity.

The first detection function may take the following form:

$$T(\langle p,cs \rangle)=P,$$

in which:

p corresponds to the physiological parameter, cs corresponds to the confidence score for the physiological parameter, P corresponds to the physiological status of the crew member.

According to the preferred embodiment, the first detection function is implemented in respect of the consolidated physiological parameter corresponding to the consolidated fatigue measurement. The first physiological status corresponds to a fatigue status. The consolidated fatigue measurement is compared against a first predetermined incapacity threshold in the comparison submodule 41.

For example, if the consolidated fatigue measurement is above or equal to the first predetermined incapacity threshold, the fatigue status adopts a value equal to 1, indicating that the crew member is considered to be suffering from fatigue. If the measurement is below the first predetermined incapacity threshold, the fatigue status adopts a value equal to 0, indicating that the crew member is considered not to be suffering from fatigue.

According to the preferred embodiment, the first detection function is also implemented in respect of the consolidated physiological parameters corresponding to the consolidated body temperature measurement and to the consolidated cardiac rhythm measurement. The first physiological statuses correspond to a febrile status and to a cardiac status. The consolidated body temperature measurement is compared against a second predetermined incapacity threshold by the comparison submodule 41. The consolidated cardiac rhythm measurement is compared against a third predetermined incapacity threshold by the comparison submodule 41.

For example, if the consolidated body temperature measurement is above or equal to the second predetermined incapacity threshold, the febrile status adopts a value equal to 1, indicating that the crew member is considered to be feverish. If the measurement is below the second predetermined incapacity threshold, the febrile status adopts a value equal to 0, indicating that the crew member is considered not to be feverish. If the consolidated cardiac rhythm measurement is above or equal to the third predetermined incapacity threshold, the cardiac status adopts a value equal to 1, indicating that the crew member is considered to have a heart problem. If the measurement is below the third predetermined incapacity threshold, the cardiac status adopts a value equal to 0, indicating that the crew member is considered not to have a heart problem.

The fusion module 4 may comprise submodules implementing a second detection function, including:

a determination DET2 submodule 43 configured to determine at least a second physiological status from at least one consolidated physiological parameter and from an inference system.

The purpose of this second function is to combine independently declared expert rules in order to determine whether the simultaneous presentation of those physiological parameters can be considered to be symptoms of a given incapacity.

The second detection function may take the following form:

$$C(\langle p_1,cs_1 \rangle, \ldots, \langle p_n,cs_n \rangle)=P,$$

in which:

$p_i$ corresponds to the physiological parameter i, $cs_i$ corresponds to the confidence score for the physiological parameter i, P corresponds to the physiological status of the crew member.

The inference system corresponds to an expert system, such as a Bayesian network or an inference machine, which comprises conditional rules and probability densities. The conditional rules and the probability densities are based on medical experiments and medical data analyses.

According to the preferred embodiment, the second detection function is implemented in respect of the consolidated physiological parameters corresponding to the consolidated head orientation measurement, to the consolidated head movement measurement, to the consolidated presence measurement, to the consolidated blink rate measurement and, possibly, to the consolidated normality measurement. The second physiological status corresponds to a first consciousness level status.

For example, the consciousness level status adopts a value equal to 1 if the consolidated head orientation measurement, the consolidated head movement measurement, the consolidated presence measurement, the consolidated blink rate measurement and, possibly, the consolidated normality measurement have values indicating to the inference system a loss of consciousness. The consciousness level status adopts a value equal to 0 if the consolidated head orientation measurement, the consolidated head movement measurement, the consolidated presence measurement, the consolidated blink rate measurement and, possibly, the consolidated normality measurement adopt values indicating to the inference system that there has not been a loss of consciousness.

The fusion module 4 may comprise submodules implementing a third detection function, including:

a computation COMPUT1 submodule 44 configured to compute a probability of good health, the probability of good health corresponding to a probability of a crew member in good health encountering the consolidated physiological parameter or parameters;

a comparison COMP2 submodule 45 configured to compare the probability of good health against at least one predetermined good health threshold;

a determination DET2 submodule 46 configured to determine at least a third physiological status on the basis of the result of the comparison obtained by the comparison submodule 45.

The third detection function corresponds to a machine anomaly detection function. The purpose of this function is to determine whether a collection of one or more physiological parameters is exhibiting abnormal values, namely that this set can be considered as being symptoms of an incapacity.

The third detection function may take the following form:

$$I(\langle p_1, cs_1 \rangle, \ldots, \langle p_n, cs_n \rangle) = p,$$

in which:

$p_i$ corresponds to the physiological parameter i, $cs_i$ corresponds to the confidence score for the physiological parameter i, p corresponds to the probability of good health.

The third function can be obtained automatically using statistical modelling techniques or machine learning techniques.

The predetermined good health threshold may be obtained by an expert judgment.

According to the preferred embodiment, the third detection function is implemented in respect of the consolidated physiological parameters corresponding to the consolidated body temperature measurement and to the consolidated cardiac rhythm measurement. The third physiological statuses correspond to a febrile status and to a cardiac status. The probability of good health for the consolidated body temperature measurement is compared against a first predetermined good health threshold by the comparison submodule 45. The probability of good health for the consolidated cardiac rhythm measurement is compared against a second predetermined good health threshold by the comparison submodule 45.

For example, if the probability of good health for the body temperature measurement is below or equal to the first predetermined good health threshold, the febrile status adopts a value equal to 1, indicating that the crew member is considered to be feverish. If the probability is above the first predetermined good health threshold, the febrile status adopts a value equal to 0, indicating that the crew member is considered not to be feverish. If the probability of good health for the consolidated cardiac rhythm measurement is below or equal to the second predetermined good health threshold, the cardiac status adopts a value equal to 1, indicating that the crew member is considered to have a heart problem. If the probability is above the second predetermined good health threshold, the cardiac status adopts a value equal to 0, indicating that the crew member is considered not to have a heart problem.

Likewise, according to the preferred embodiment, the third detection function is implemented in respect of the consolidated physiological parameters corresponding to the consolidated head orientation measurement, to the consolidated head movement measurement, to the consolidated presence measurement, to the consolidated blink rate measurement, and, possibly, to the consolidated normality measurement. The third physiological status corresponds to a second consciousness level status.

According to a first alternative form, the probabilities of good health are computed for each of the measurements by the computation submodule 44. The probability of good health for the consolidated head orientation measurement is compared against a third predetermined good health threshold by the comparison submodule 45. The probability of good health for the consolidated head movement measurement is compared against a fourth predetermined good health threshold in the comparison submodule 45. The probability of good health for the consolidated presence measurement is compared against a fifth predetermined good health threshold by the comparison submodule 45. The probability of good health for the consolidated blink rate measurement is compared against a sixth predetermined good health threshold by the comparison submodule 45. Possibly, the probability of good health for the consolidated normality measurement is compared against a seventh predetermined good health threshold in the comparison submodule 45.

For example, the consciousness level status adopts a value equal to 1, indicating a loss of consciousness of the crew member:

if the probability of good health for the consolidated head orientation measurement is below or equal to the third good health threshold, and if the probability of good health for the consolidated head movement measurement is below or equal to the fourth good health threshold, and if the probability of good health for the consolidated presence measurement is below or equal to the fifth predetermined good health threshold, and if the probability of good health for the consolidated blink rate measurement is below or equal to the sixth predetermined good health threshold, and if appropriate, if the probability of good health for the consolidated normality measurement is below or equal to the seventh predetermined good health threshold.

If not, the consciousness level status adopts a value equal to 0, indicating a non-loss of consciousness of the crew member.

According to a second alternative form, a first overall good health probability is determined by the computation submodule 44 on the basis of the probability of good health for the consolidated head orientation measurement, of the probability of good health for the consolidated head movement measurement, of the probability of good health for the consolidated presence measurement, of the probability of good health for the consolidated blink rate measurement, and, where appropriate, of the probability of good health for the consolidated normality measurement. The probabilities of good health pertaining to these measurements are computed by the computation submodule 44. The first overall good health probability is compared against a first predetermined overall good health threshold by the comparison submodule 45. The consciousness level status adopts a value equal to 1, indicating the loss of consciousness of the crew member if the first overall good health probability is below or equal to the first overall good health threshold. If not, the consciousness level status adopts a value equal to 0, indicating a non-loss of consciousness of the crew member.

In addition, according to the preferred embodiment, the third detection function is implemented in respect of the consolidated physiological parameters corresponding to the fatigue measurement, to the body temperature measurement, to the cardiac rhythm measurement, to the consolidated head orientation measurement, to the consolidated head movement measurement, to the consolidated presence measurement, to the consolidated blink rate measurement, to the measurement of the movement of the crew member and, where appropriate, to the consolidated normality measurement. The third physiological status corresponds to a status of incapacity of the crew member.

According to a first alternative form, the probabilities of good health are computed for each of the measurements by the computation submodule 44. The probability of good health for the consolidated body temperature measurement is compared against an eighth predetermined good health threshold by the comparison submodule 45. The probability of good health for the consolidated cardiac rhythm measurement is compared against a ninth predetermined good health threshold by the comparison submodule 45. The probability of good health for the consolidated head orientation measurement is compared against a tenth predetermined good health threshold by the comparison submodule 45. The probability of good health for the consolidated head movement measurement is compared against an eleventh predetermined good health threshold by the comparison submodule 45. The probability of good health for the consolidated presence measurement is compared against a twelfth predetermined good health threshold by the comparison submodule 45. The probability of good health for the consolidated blink rate measurement is compared against a thirteenth predetermined good health threshold by the comparison submodule 45. The probability of good health for the consolidated crew member movement measurement is compared against a fourteenth predetermined good health threshold by the comparison submodule 45. Where appropriate, the probability of good health for the consolidated normality measurement is compared against a fifteenth predetermined good health threshold by the comparison submodule 45.

For example, the incapacity status adopts a value equal to 1 indicating the incapacity of the crew member to perform:

if the probability of good health for the consolidated body temperature measurement is above or equal to the eighth good health threshold, and if the probability of good health for the consolidated cardiac rhythm measurement is above or equal to the ninth good health threshold, and if the probability of good health for the consolidated head orientation measurement is above or equal to the tenth predetermined good health threshold, and if the probability of good health for the consolidated head movement measurement is above or equal to the eleventh predetermined good health threshold, and if the probability of good health for the consolidated presence measurement is above or equal to the twelfth predetermined good health threshold, and if the probability of good health for the consolidated blink rate measurement is above or equal to the thirteenth predetermined good health threshold, and if the probability of good health for the consolidated crew member movement measurement is above or equal to the fourteenth predetermined good health threshold, and where appropriate, if the probability of good health for the consolidated normality measurement is above or equal to the fifteenth predetermined good health threshold.

If not, the incapacity status adopts a value equal to 0, indicating that the crew member does have the capacity to perform.

According to a second alternative form, a second overall good health probability is determined by the computation submodule 44 on the basis of the probability of good health for the consolidated body temperature measurement, of the probability of good health for the consolidated cardiac rhythm measurement, of the probability of good health for the consolidated head orientation measurement, of the probability of good health for the consolidated head movement measurement, of the probability of good health for the consolidated presence measurement, the probability of good health for the consolidated blink rate measurement, of the probability of good health for the consolidated crew member movement measurement and, where appropriate, of the probability of good health for the consolidated normality measurement. The probabilities of good health for these measurements are computed by the computation submodule 44. The second overall good health probability is compared against a second predetermined overall good health threshold by the comparison submodule 45. The incapacity status adopts a value equal to 1, indicating the incapacity of the crew member to perform if the second overall good health probability is below or equal to the second overall good health threshold. If not, the incapacity status adopts a value equal to 0, indicating that the crew member does have the capacity to perform.

The monitoring device 1 may also comprise a filtration FILT module 5, configured to filter the physiological status or statuses detected by the fusion module 4 in order to retain the most probable physiological status or statuses. The purpose of the filtration module 5 is to limit spurious alerts.

The filtration module 5 is based on a filtration function which may take the following form:

$$TCS(\{F(I), F(cs_i, cs_n)\}) = I',$$

in which:

F corresponds to one of the detection functions,

I corresponds to the physiological status detected by one of the detection functions, $cs_i$, $cs_n$ corresponds to the confidence scores for the physiological parameters used by the detection function in order to determine I, I' corresponds to the physiological status of the crew member.

The filtration device may comprise the following submodules:

a computation COMPUT2 submodule 51 configured to compute a mean of the confidence score or scores for each of the physiological status detection functions, the confidence score or scores being associated with the measurement module or modules configured to measure the physiological parameter or parameters used by the physiological status detection function;

a comparison COMP3 submodule 52 configured to compare the mean computed in the second computation substep against a predetermined confidence score threshold;

a determination DET4 substep 53, implemented by a fourth determination submodule, comprising determining the most probable physiological status or statuses on the basis of the result of the comparison in the third comparison substep.

Filtration makes it possible to reject the physiological statuses that are significantly unreliable.

The mean of the confidence scores may correspond to an arithmetic mean, to a harmonic mean, to a median, etc. It is defined by an expert on the basis of medical experiments, medical data analyses, or by an expert judgment.

The filtration threshold may take the form of conditional rules, and may be defined by an expert on the basis of medical experiments, medical data analyses, or by an expert judgment.

The monitoring device 1 also comprises a determination DET module 6, configured to determine a level of incapacity of the crew member on the basis of the most probable physiological status or statuses determined by the filtration module 5.

Nonlimitingly, the incapacity level may correspond to two degrees of alertness: a degree of partial alertness and a degree of full alertness. Each of the degrees may adopt a binary value.

The determination module 6 combines the filtered physiological statuses in order to determine the effective degree of alertness. For example, a degree of alertness is effective when it adopts a value equal to 1. If not it adopts a value equal to 0.

By way of example, the degree of partial alertness is equal to 1 if at least one of the following physiological statuses adopts a value equal to 1: the fatigue status, the febrile status, the incapacity status. The degree of partial alertness is equal to 0 if all these physiological statuses adopt values equal to 0. The degree of total alertness is equal to 1 if at least one of the following physiological statuses has a value equal to 1: the cardiac status, the consciousness level status, the incapacity status. The degree of total alertness is equal 0 if all these physiological statuses adopt values equal to 0.

A transmission TRANS module 7 that forms part of the monitoring device 1 is configured to transmit to a user USER module 8 a signal indicative of the level of incapacity of the crew member.

The user module 8 may be a display device.

The invention also relates to a method for monitoring the incapacity of a crew member of an aircraft AC.

Figure 2:
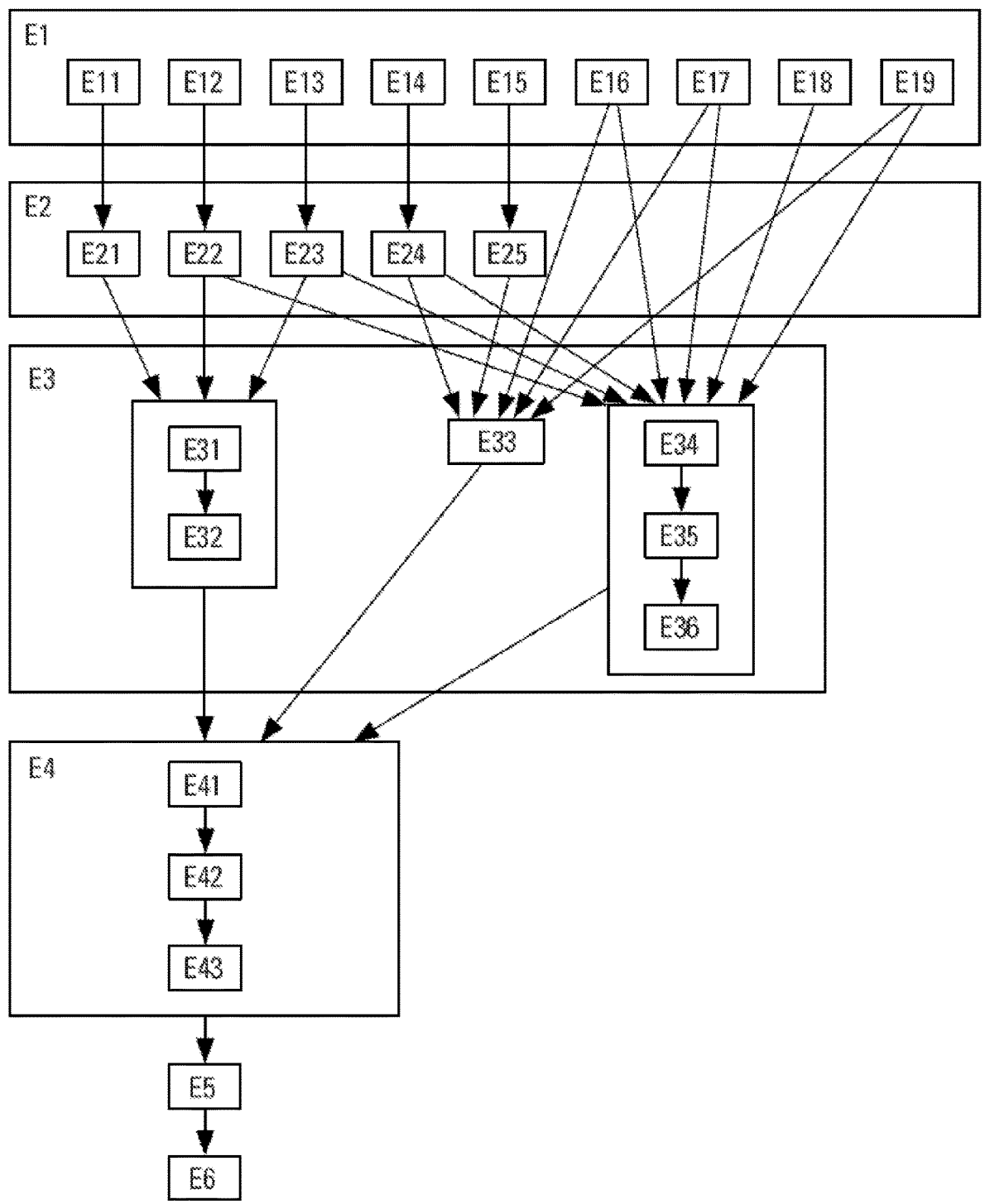
FIG. 2 depicts one embodiment of the monitoring method.

The monitoring method comprises the following steps (FIG. 2):

a measurement step E1, which is implemented by the measurement module or modules 2, comprising measuring at least one physiological parameter regarding the crew member and in supplying at least one associated confidence score to the measurement module or modules 2 respectively;

a consolidation step E2, which is implemented by the consolidation module or modules 3, comprising consolidating the measured physiological parameter or parameters and in determining the consolidated confidence score or scores regarding the consolidated physiological parameter or parameters;

a fusion step E3, which is implemented by the fusion module 4, comprising fusing the consolidated physiological parameter or parameters so as to detect at least one physiological status of the crew member from at least one physiological status detection function;

a filtering step E4, which is implemented by the filtering module 5, comprising filtering the physiological status or statuses detected in the fusion step E3 so as to retain the most probable physiological status or statuses;

a determination step E5, which is implemented by the determination module 6, comprising determining a level of incapacity of the crew member from the most probable physiological status or statuses determined in the filtering step;

a transmission step E6, which is implemented by the transmission module 7, comprising transmitting to a user module 8 a signal indicative of the level of incapacity of the crew member.

The fusion step E3 may comprise substeps of the first detection function, including:

a comparison substep E31, implemented by the comparison submodule 41, comprising comparing at least one consolidated physiological parameter against at least one predetermined incapacity threshold;

a determination substep E32, implemented by the determination submodule 42, comprising determining at least a first physiological status on the basis of the result of the comparison of the comparison substep E31.

The fusion step E3 may also comprise substeps of the second detection function, including:

a determination substep E33, implemented by the determination submodule 43, comprising determining at least a second physiological status from at least one consolidated physiological parameter and from an inference system comprising conditional rules and probability densities, the conditional rules and the probability densities being based on medical experiments and medical data analyses.

The fusion step E3 may also comprise substeps of the third detection function, including:

a computation substep E34, implemented by the computation submodule 44, comprising computing a probability of good health, the probability of good health corresponding to a probability of a crew member in good health encountering the consolidated physiological parameters;

a comparison substep E35, implemented by the comparison submodule 45, comprising comparing the probability of good health against at least one predetermined good health threshold;

a determination substep E36, implemented by the determination submodule 46, comprising determining at least a third physiological status on the basis of the result of the comparison of the comparison substep E35.

The filtration step E4 may also comprise the following substeps:

a computation substep E41, implemented by the computation submodule 51, comprising computing a mean of the confidence score or scores for each of the physiological status detection functions, the confidence score or scores being associated with the measurement module or modules 2 configured to measure the physiological parameter or parameters used by the physiological status detection function;

a comparison substep E42, implemented by the comparison submodule 52, comprising comparing the mean computed in the computation substep E41 against a predetermined confidence score threshold;

a determination substep E43, implemented by the determination submodule 53, comprising determining the most probable physiological status or statuses on the basis of the result of the comparison of the comparison substep E42.

According to the preferred embodiment, the measurement step E1 comprises the following substeps:

a substep E11 of measuring fatigue, which is implemented by the fatigue measurement module 211 located in the headset configured to be donned by the crew member and by the fatigue measurement module 212 located in the first video equipment configured to capture images of the crew member, comprising capturing measurements of the fatigue of the crew member;

a substep E12 of measuring cardiac rhythm, which is implemented by the cardiac rhythm measurement module 221 located in the headset, the cardiac rhythm measurement module 222 located in the first video equipment and the cardiac rhythm measurement module 223 located in a seat configured to accept the crew member, comprising capturing measurements of the cardiac rhythm of the crew member;

a substep E13 of measuring body temperature, which is implemented by the body temperature measurement module 231 located in the headset, the body temperature measurement module 232 located in the first video equipment, and the body temperature measurement module 233 located in the seat, comprising capturing measurements of the body temperature of the crew member;

a substep E14 of measuring head orientation, which is implemented by the head orientation measurement module 241 located in the headset and the head orientation measurement module 242 located in the first video equipment, comprising capturing measurements of the orientation of the head of the crew member;

a substep E15 of measuring head movement, which is implemented by the head movement measurement module 251 located in the headset and the head movement measurement module 252 located in the first video equipment, comprising capturing measurements of the movement of the head of the crew member;

a substep E16 of measuring blink rate, which is implemented by the ocular measurement module 261 located in the first video equipment, comprising capturing measurements of the frequency at which the crew member blinks;

a substep E17 of measuring presence, which is implemented by the presence measurement module 271 located in the first video equipment, comprising capturing measurements of the presence of the crew member;

a substep E18 of measuring movement, which is implemented by the movement measurement module 281 located in the seat, comprising capturing measurements of the movement of the crew member;

if appropriate, a substep E19 of measuring normality, which is implemented by the normality measurement module 291 located in the second video equipment, comprising capturing measurements of the normality of a scene in which the crew member is supposed to appear.

According to the preferred embodiment, the consolidation step E2 comprises the following substeps:

a substep E21 of consolidating the measured fatigue, which is implemented by the consolidation submodule 31, comprising determining a consolidated fatigue measurement from the fatigue measurements captured in the fatigue measurement substep E11;

a substep E22 of consolidating the measured cardiac rhythm, which is implemented by the consolidation submodule 32, comprising determining a consolidated cardiac rhythm measurement from the cardiac rhythm measurements captured in the cardiac rhythm measurement substep E12;

a substep E23 of consolidating the measured body temperature, which is implemented by the consolidation submodule 33, comprising determining a consolidated body temperature measurement from the body temperature measurements captured in the body temperature measurement substep E13;

a substep E24 of consolidating the measured head orientation, which is implemented by the consolidation submodule 34, comprising determining a consolidated head orientation measurement from the head orientation measurements captured in the head orientation measurement substep E14;

a substep E25 of consolidating the measured head movement, which is implemented by the consolidation submodule 35, comprising determining a consolidated head movement measurement from the head movement measurements captured in the head movement measurement substep E15.

According to the preferred embodiment, the substeps E31, E32 of the first detection function are implemented in respect of the consolidated physiological parameter corresponding to the consolidated fatigue measurement. The consolidated fatigue measurement is compared against the first predetermined incapacity threshold in the comparison substep E31.

According to the preferred embodiment, the substeps E31, E32 of the first detection function are implemented in respect of the consolidated physiological parameters corresponding to the consolidated body temperature measurement and to the consolidated cardiac rhythm measurement. The consolidated body temperature measurement is compared against the second predetermined incapacity threshold in the comparison substep E31. Likewise, the consolidated cardiac rhythm measurement is compared against the third predetermined incapacity threshold in the first comparison substep E31.

According to the preferred embodiment, the substeps E33 of the second detection function are implemented in respect of the consolidated physiological parameters corresponding to the consolidated head orientation measurement, to the consolidated head movement measurement, to the consolidated presence measurement, to the consolidated blink rate measurement and, where appropriate, to the consolidated normality measurement.

According to the preferred embodiment, the substeps E34, E35, E36 of the third description function are implemented in respect of the consolidated physiological parameters corresponding to the consolidated body temperature measurement and to the consolidated cardiac rhythm measurement. The probability of good health for the consolidated body temperature measurement is compared against the first predetermined good health threshold in the comparison substep E35. The probability of good health for the consolidated cardiac rhythm measurement is compared against the second predetermined good health threshold in the comparison substep E35.

According to a first alternative form of the preferred embodiment, the substeps E34, E35, E36 of the third detection function are implemented in respect of the consolidated physiological parameters corresponding to the consolidated head orientation measurement, to the consolidated head movement measurement, to the consolidated presence measurement, to the consolidated blink rate measurement and to the consolidated normality measurement. The probability of good health for the consolidated head orientation measurement is compared against the third predetermined good health threshold in the comparison substep E35. The probability of good health for the consolidated head movement measurement is compared against the fourth predetermined good health threshold in the comparison substep E35. The probability of good health for the consolidated presence measurement is compared against the fifth predetermined good health threshold in the comparison substep E35. The probability of good health for the consolidated blink rate measurement is compared against the sixth predetermined good health threshold in the comparison substep E35. Where appropriate, the probability of good health for the consolidated normality measurement is compared against the seventh predetermined good health threshold in the comparison substep E35.

According to a second alternative form of the preferred embodiment, the substeps E34, E35, E36 of the third detection function are implemented in respect of the consolidated physiological parameters corresponding to the consolidated head orientation measurement, to the consolidated head movement measurement, to the consolidated presence measurement, to the consolidated blink rate measurement and, where appropriate, to the consolidated normality measurement. The first overall good health probability is determined in the substep E34 from the probability of good health for the consolidated head orientation measurement, from the probability of good health for the consolidated head movement measurement, from the probability of good health for the consolidated presence measurement, from the probability of good health for the consolidated blink rate measurements, and, where appropriate, from the probability of good health for the consolidated normality measurement. The first overall good health probability is compared against the first predetermined good health probability in the substep E35.

According to a first alternative form for the preferred embodiment, the substeps E34, E35, E36 of the third detection function are implemented for the consolidated physiological parameters corresponding to the fatigue measurement, to the body temperature measurement, to the cardiac rhythm measurement, to the consolidated head orientation measurement, to the consolidated head movement measurement, to the consolidated presence measurement, to the consolidated blink rate measurement, to the crew member movement measurement and, where appropriate, to the consolidated normality measurement. The probability of good health for the consolidated body temperature measurement is compared against the eighth predetermined good health threshold in the comparison substep E35. The probability of good health for the consolidated cardiac rhythm measurement is compared against the ninth predetermined good health threshold in the comparison substep E35. The probability of good health for the consolidated head orientation measurement is compared against the tenth predetermined good health threshold in the comparison substep E35. The probability of good health for the consolidated head movement measurement is compared against the eleventh predetermined good health threshold in the comparison substep E35. The probability of good health for the consolidated presence measurement is compared against the twelfth predetermined good health threshold in the comparison substep E35. The probability of good health for the consolidated blink rate measurement is compared against the thirteenth predetermined good health threshold in the comparison substep E35. The probability of good health for the consolidated crew member movement measurement is compared against the fourteenth predetermined good health threshold in the comparison substep E35. Where appropriate, the probability of good health for the consolidated normality measurement is compared against the fifteenth predetermined good health threshold in the comparison substep E35.

According to a second alternative form of the preferred embodiment, the substeps E34, E35, E36 of the third detection function are implemented for the consolidated physiological parameters corresponding to the fatigue measurement, to the body temperature measurement, to the cardiac rhythm measurement, to the consolidated head orientation measurement, to the consolidated head movement measurement, to the consolidated presence measurement, to the consolidated blink rate measurement, to the crew member movement measurement and, where appropriate, to the consolidated normality measurement. The second overall good health probability is determined in the substep E34 from the probability of good health for the consolidated body temperature measurement, from the probability of good health for the consolidated cardiac rhythm measurement, from the probability of good health for the consolidated head orientation measurement, from the probability of good health for the consolidated head movement measurement, from the probability of good health for the consolidated presence measurement, from the probability of good health for the consolidated blink rate measurement, from the probability of good health for the consolidated crew member movement measurement and, where appropriate, from the probability of good health for the consolidated normality measurement. The second overall good health probability is compared against the second predetermined overall good health threshold in the substep E35. The incapacity status adopts a value equal to 1 indicating an incapacity of the crew member to perform if the second overall good health probability is below or equal to the second overall good health threshold. If not, the incapacity status adopts a value equal to 0 indicating that the crew member does have the capacity to perform.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A method for monitoring a capacity of a crew member of an aircraft, comprising the following steps:
   measuring, by at least one measurement module comprising a sensor, a probe, a camera, or a combination thereof, at least one physiological parameter regarding the crew member;

supplying an associated confidence score for the measurement measured by the at least one measurement module;

consolidating the measurement measured by the at least one measurement module and the associated confidence score to determine a consolidated physiological parameter and consolidated confidence score regarding the consolidated physiological parameter;

fusing the consolidated physiological parameter to detect at least one physiological status of the crew member and assigning a binary value to the at least one physiological status;

filtering the at least one physiological status detected in the fusion step based in part on the binary value assigned to the at least one physiological status to retain a most probable physiological status;

determining a level of incapacity of the crew member from the most probable physiological status determined in the filtering step; and, transmitting to a user module a signal indicative of the level of incapacity of the crew member.

2. The method according to claim 1, wherein the fusion step comprises substeps of a first detection function, including:

a first comparison substep comprising comparing at least one consolidated physiological parameter against at least one predetermined incapacity threshold; and a first determination substep comprising determining at least a first physiological status on a basis of a result of the comparison of the first comparison substep.

3. The method according to claim 1, wherein the fusion step comprises substeps of a second detection function, including:

a second determination substep comprising determining at least a second physiological status from at least one consolidated physiological parameter and from an inference system comprising conditional rules and probability densities, the conditional rules and the probability densities being based on medical experiments and analysis of medical data.

4. The method according to claim 1, wherein the fusion step comprises substeps of a third detection function, including:

a first computation substep comprising computing a probability of good health, the probability of good health corresponding to a probability of a crew member in good health encountering the consolidated physiological parameter or parameters;

a second comparison substep comprising comparing the probability of good health against at least one predetermined good health threshold; and a third determination substep comprising determining at least one third physiological status on a basis of a result of the comparison of the second comparison substep.

5. The method according to claim 1, wherein the filtering step comprises the following substeps:

a second computation substep comprising computing a mean of the at least one confidence score for the at least one physiological status detection function, the confidence score being associated with the measurement module configured to measure the at least one physiological parameter used by the physiological status detection function;

a third comparison substep comprising comparing the mean calculated in the second computation substep against a predetermined confidence score threshold; and a fourth determination substep comprising determining a most probable physiological status based on a result of the comparison of the third comparison substep.

6. The method according to claim 1, wherein the measurement step comprises the following substeps:

a substep of measuring fatigue, implemented by a first fatigue measurement module located in a headset configured to be donned by the crew member and by a second fatigue measurement module located in a first video equipment configured to capture images of the crew member, comprising capturing measurements of the fatigue of the crew member;

a substep of measuring cardiac rhythm, which is implemented by a first cardiac rhythm measurement module located in the headset, a second cardiac rhythm measurement module located in the first video equipment and a third cardiac rhythm measurement module located in a seat configured to accept the crew member, comprising capturing measurements of the cardiac rhythm of the crew member;

a substep of measuring body temperature, which is implemented by a first body temperature measurement module located in the headset, a second body temperature measurement module located in the first video equipment and a third body temperature measurement module located in the seat, comprising capturing measurements of the body temperature of the crew member;

a substep of measuring head orientation, which is implemented by a first head orientation measurement module located in the headset and a second head orientation measurement module located in the first video equipment, comprising capturing measurements of the orientation of a head of the crew member;

a substep of measuring head movement, which is implemented by a first head movement measurement module located in the headset and a second head movement measurement module located in the first video equipment, comprising capturing measurements of the movement of the head of the crew member;

a substep of measuring blink rate, which is implemented by an ocular measurement module located in the first video equipment, comprising capturing measurements of a frequency at which the crew member blinks;

a substep of measuring presence, which is implemented by a presence measurement module located in the first video equipment, comprising capturing measurements of the presence of the crew member;

a substep of measuring movement, which is implemented by a movement measurement module located in the seat, comprising capturing measurements of the movement of the crew member.

7. The method according to claim 6, wherein the consolidation step comprises the following substeps:

a sub step of consolidating the measured fatigue comprising determining a consolidated fatigue measurement from the fatigue measurements captured in the fatigue measurement substep;

a substep of consolidating the measured cardiac rhythm comprising determining a consolidated measurement for cardiac rhythm from the cardiac rhythm measurements captured in the cardiac rhythm measurement substep;

a sub step of consolidating the measured body temperature comprising determining a consolidated body temperature measurement from the body temperature measurements captured in the body temperature measurement substep;

a substep of consolidating the measured head orientation comprising determining a consolidated head orientation measurement from the head orientation measurements captured in the head orientation measurement sub step;

a substep of consolidating measured head movement comprising determining a consolidated head movement measurement from the head movement measurements captured in the head movement measurement substep.

8. The method according to claim 6,
wherein the fusion step comprises substeps of a first detection function, including:
   a first comparison substep comprising comparing at least one consolidated physiological parameter against at least one predetermined incapacity threshold; and
   a first determination substep comprising determining at least a first physiological status on a basis of a result of the comparison of the first comparison substep, and
wherein the substeps of the first detection function are implemented in respect of the consolidated physiological parameter corresponding to the consolidated fatigue measurement,
the first physiological status corresponding to a fatigue status,
the consolidated fatigue measurement being compared against a first predetermined incapacity threshold in the first comparison substep.

9. The method according to claim 6,
wherein the fusion step comprises substeps of a first detection function, including:
   a first comparison substep comprising comparing at least one consolidated physiological parameter against at least one predetermined incapacity threshold; and
   a first determination substep comprising determining at least a first physiological status on a basis of a result of the comparison of the first comparison substep, and
wherein the substeps of the first detection function are implemented in respect of the consolidated physiological parameters corresponding to the consolidated body temperature measurement and to the consolidated cardiac rhythm measurement,
the first physiological statuses corresponding to a febrile status and to a cardiac status,
the consolidated body temperature measurement being compared against a second predetermined incapacity threshold in the first comparison substep,
the consolidated cardiac rhythm measurement being compared against a third predetermined incapacity threshold in the first comparison substep.

10. The method according to claim 6,
wherein the fusion step comprises substeps of a third detection function, including:
   a first computation substep comprising computing a probability of good health, the probability of good health corresponding to a probability of a crew member in good health encountering the consolidated physiological parameter or parameters;
   a second comparison substep comprising comparing the probability of good health against at least one predetermined good health threshold; and
   a third determination substep comprising determining at least one third physiological status on a basis of a result of the comparison of the second comparison substep,
wherein the substeps of the third detection function are implemented in respect of the consolidated physiological parameters corresponding to the consolidated body temperature measurement and to the consolidated cardiac rhythm measurement,
the third physiological statuses corresponding to a febrile status and to a cardiac status,
the probability of good health for the consolidated body temperature measurement being compared against a first predetermined good health threshold in the second comparison substep,
the probability of good health for the consolidated cardiac rhythm measurement being compared against a second predetermined good health threshold in the second comparison substep.

11. The method according to claim 6,
wherein the fusion step comprises substeps of a second detection function, including:
   a second determination substep comprising determining at least a second physiological status from at least one consolidated physiological parameter and from an inference system comprising conditional rules and probability densities, the conditional rules and the probability densities being based on medical experiments and analysis of medical data,
wherein the substeps of the second detection function are implemented in respect of the consolidated physiological parameters corresponding to the consolidated head orientation measurement, to the consolidated head movement measurement, to the consolidated presence measurement and to the consolidated blink rate measurement,
the second physiological status corresponding to a first consciousness level status.

12. The method according to claim 6,
wherein the fusion step comprises substeps of a third detection function, including:
   a first computation substep comprising computing a probability of good health, the probability of good health corresponding to a probability of a crew member in good health encountering the consolidated physiological parameter or parameters;
   a second comparison substep comprising comparing the probability of good health against at least one predetermined good health threshold; and
   a third determination substep comprising determining at least one third physiological status on a basis of a result of the comparison of the second comparison substep,
wherein the substeps of the third detection function are implemented in respect of the consolidated physiological parameters corresponding to the consolidated head orientation measurement, to the consolidated head movement measurement, to the consolidated presence measurement and to the consolidated blink rate measurement,
the third physiological status corresponding to a second consciousness level status,
a first probability of good overall health being determined in the first computation substep from a probability of good health for the consolidated head orientation measurement, a probability of good health for the consolidated head movement measurement, a probability of good health for the consolidated presence measurement and a probability of good health for the consolidated blink rate measurement, the first probability of overall good health being compared in the second comparison substep against a first predetermined overall good health threshold.

13. The method according to claim 6,
wherein the fusion step comprises substeps of a third detection function, including:
- a first computation substep comprising computing a probability of good health, the probability of good health corresponding to a probability of a crew member in good health encountering the consolidated physiological parameter or parameters;
- a second comparison substep comprising comparing the probability of good health against at least one predetermined good health threshold; and
- a third determination substep comprising determining at least one third physiological status on a basis of a result of the comparison of the second comparison substep, wherein the substeps of the third detection function are implemented in respect of the consolidated physiological parameters corresponding to the fatigue measurement, to the body temperature measurement, to the cardiac rhythm measurement, to the consolidated head orientation measurement, to the consolidated head movement measurement, to the consolidated presence measurement, to the consolidated blink rate measurement and to the measurement of the movement of the crew member, the third physiological status corresponding to a crew member incapacity status, a second probability of overall good health is determined in the first computation substep from a probability of good health for the consolidated body temperature measurement, a probability of good health for the consolidated cardiac rhythm measurement, a probability of good health for the consolidated head orientation measurement, a probability of good health for the consolidated head movement measurement, a probability of good health for the consolidated presence measurement, a probability of good health for the consolidated blink rate measurement and a probability of good health for the consolidated measurement of the movement of the crew member, the second probability of overall good health being compared in the second comparison step against a second predetermined overall good health threshold.

* * * * *